United States Patent [19]

Beale

[11] 4,305,399
[45] Dec. 15, 1981

[54] MINIATURE TRANSDUCER

[75] Inventor: David G. Beale, Kalamunda, Australia

[73] Assignee: The University of Western Australia, Nedlands, Australia

[21] Appl. No.: 175,040

[22] Filed: Aug. 4, 1980

Related U.S. Application Data

[63] Continuation of Ser. No. 956,362, Oct. 31, 1978, abandoned.

[51] Int. Cl.³ ............................ A61B 3/16; A61B 5/00
[52] U.S. Cl. .................................... 128/645; 128/635; 128/748; 73/728; 336/118; 336/115
[58] Field of Search ............... 128/645, 646, 635, 652, 128/653, 676, 745, 748; 73/722, 728; 336/115–118

[56] References Cited

U.S. PATENT DOCUMENTS

| | | | |
|---|---|---|---|
| 2,621,224 | 12/1952 | Priest | 336/117 X |
| 2,722,662 | 11/1955 | Tyminski | 336/115 X |
| 2,788,664 | 4/1957 | Coulbourn et al. | 73/728 |
| 3,189,023 | 6/1965 | Salz et al. | 73/722 X |
| 3,769,961 | 11/1973 | Fatt et al. | 128/635 |
| 3,827,291 | 8/1974 | McCalvey | 336/115 X |
| 3,893,444 | 7/1975 | Fatt | 128/635 |
| 3,958,560 | 5/1976 | March | 128/633 |

OTHER PUBLICATIONS

*RCA Technical Notes*, No. 602, Dec. 1964, pp. 1 & 2.
Collins, C. C., IEEE Trans. on Bio.-Med. Engng., vol. BME-14, No. 2, Apr., 1967, pp. 74–83.

*Primary Examiner*—Kyle L. Howell
*Attorney, Agent, or Firm*—Oblon, Fisher, Spivak, McClelland & Maier

[57] ABSTRACT

A pressure or force transducer capable of miniaturization. Preferably, the transducer takes the form of a "contact lens" and is applied to the eyeball to permit intra-ocular pressure to be measured.

12 Claims, 1 Drawing Figure

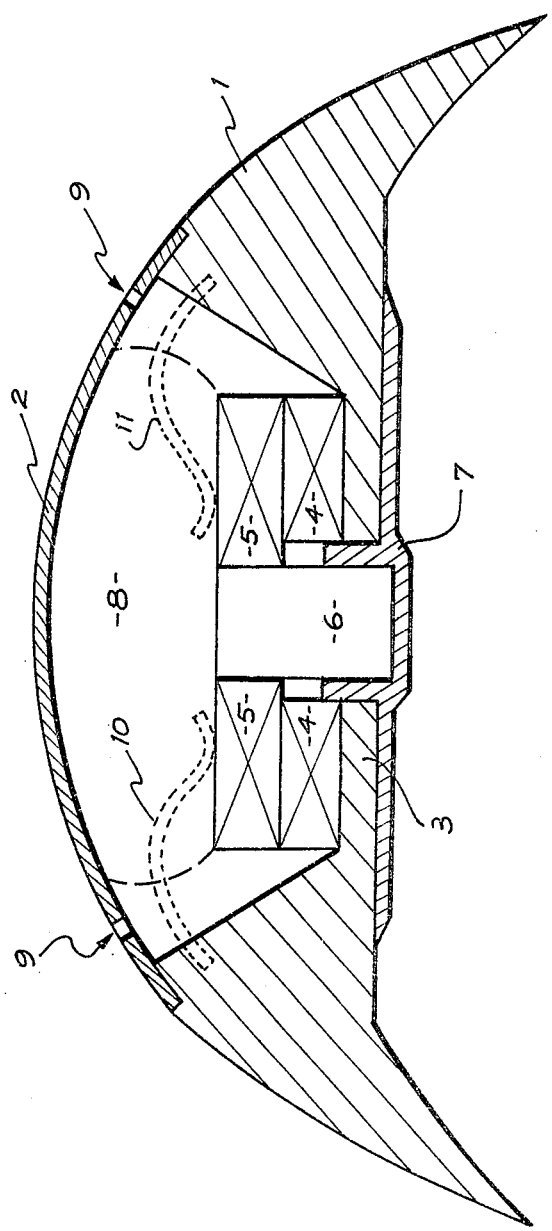

MINIATURE TRANSDUCER

This is a continuation of application Ser. No. 956,362, filed Oct. 31, 1978, now abandoned.

The present invention relates to a miniature transducer which finds particular application in ophthalmic measurements and, in particular, in the measurement of intra-ocular pressure in vivo. Accordingly, the present invention finds application in the accurate diagnosis and management of glaucomas.

Although the present invention is particularly suited for ophthalmic applications, the invention is not limited thereto and may be used in other fields. For example if the transducer is encapsulated in a pH-swelling plastic then the transducer may be used to sense the acidity or alkalinity of a solution. Since the transducer may be made small enough to be swallowed like a pill, the solution may be an intestinal solution. Similarly the transducer may be arranged in conjunction with a bimetal or biplastic strip so as to measure temperature. However in its basic form the transducer responds directly to pressure or force.

The measurement of intra-ocular pressure has been attempted in many ways. In U.S. Pat. Nos. 3,893,444 and 3,769,961 a telemetry system for measuring biological conditions within the eye is disclosed which system requires external electrical leads to extend from the eye. Such a system clearly places restrictions on the mobility of the patient and gives rise to other consequent disadvantages. U.S. Patent Application Ser. No. 668,020 discloses a transducer which is located in or on the eye and connected to a transmitter by wires. However, the transmitter is located on the patient near to the eye. Therefore, the transmitter and transducer are carried by the patient and the mobility of the patient is not restricted. However, the cost and complexity of such an arrangement constitute substantial disadvantages.

In addition, U.S. Pat. No. 3,958,560 discloses the transmission of infrared radiation through the eye. The infrared transmitter is located to one side of the eye and the infrared receiver is positioned to the other side of the eye. In addition a power source and a data transmitter are all located at the eye. Therefore, this arrangement provides an extremely complicated and expensive solution to the problem of measuring biological conditions within the eye.

R.C.A. Technical Note No. 602 of December 1964 discloses three different forms of transducer adapted to be located on or in the eye. The first of these forms comprises a resonant circuit formed from a single coil and a single capacitor and a magnet which is movable relative to the resonant circuit. The second form comprises a magnet and a single coil both of which are subjected to an external magnetic field. The third form of transducer comprises a pressure sensitive transistor and complicated electronic circuitry to provide an operating circuit for the transistor.

The foregoing prior art transducers suffer from disadvantages such as lack of mobility of the patient, undue cost or complexity of the transducer, or lack of sufficient resolution and/or accuracy. Accordingly it is the object of the present invention to provide a relatively uncomplicated transducer which may be provided at low cost and which gives adequate performance.

According to one aspect of the present invention there is disclosed a transducer comprising first and second coils having a common permeable core, said second coil being secured to a fixed member, said first coil and said core being secured together and movable relative to said fixed member, and resilient mounting means supporting said first coil and said core and urging same into a rest position relative to said fixed member in the absence of a force applied to said first coil and/or core.

Preferably the abovementioned fixed member comprises a housing for the transducer and, in addition, the first and second coils are preferably touching in the rest position.

Embodiments of the present invention will now be described with reference to the drawing which shows a schematic cross-sectional view of an elliptical contact lens incorporating the pressure transducer.

The housing 1 for the transducer comprises a cup-shaped "contact lens" formed from conventional materials such as hydrogel or polymethyl methacrylate. The housing 1 is covered by a curved front cover 2 which forms the outwardly directed surface of the transducer. Accordingly, the front cover 2 comes into contact with the inner surface of the eye lid whilst the generally concave surface of the housing 1 is applied to the surface of the eye. The front cover 2 is preferably formed from polymethyl methacrylate and glued to the housing 1 by synthetic rubber.

The interior of the housing 1 is shaped so as to provide an annular shelf 3 which provides a fixed support for the transducer. An inner coil 4 is glued to the shelf 3 and is wound in one or more layers parallel to the shelf 3 with turns substantially concentric with the opening in the shelf 3. The outer uppermost winding of the inner coil 4 preferably continues to form the outer most winding of the single layer, or lowermost layer, of outer coil 5 which normally rests on the inner coil 4. Both coils 4 and 5 are wound in the same sense and are wound for maximum capacitance. The coils 4 and 5 are flat or planar and are encapsulated, preferably in an acrylic denture moulding compound.

The outer coil 5 is glued to a permeable core 6 which preferably comprises finely ground ferrite material embedded in acrylic glue or other adhesive. The core 6 takes the form of a cylinder which extends through both coils 4 and 5. Therefore, the core 6 provides a common permeable core for both coils. Other permeable materials such as conventional ferrites could be used for the core 6.

The outer coil 5 and core 6 are mounted for movement relative to the inner coil 4 and shelf 3 by means of a membrane 7 of synthetic rubber or similar material which covers the inwardly directed end of the core 6, the inwardly directed surface of the shelf 3, and extends part way into the annular gap formed between the inner coil 4 and the core 6.

When no force is applied to the core 6 or outer coil 5, the membrane 7 urges the outer coil 5 into its rest position in which it touches the inner coil 4. When the transducer is positioned on the surface of the eye, the core 6 is subjected to the intra-ocular pressure via the eyeball and therefore moves the outer coil 5 away from the inner coil 4.

The separation of the coils 4 and 5 alters the natural resonant frequency of the coils 4 and 5 and therefore this resonant frequency is dependent upon the intra-ocular pressure. Over physiological ranges this relationship is substantially linear. The measurement of the resonant frequency of the transducer coils may be performed by any method including the known use of a grid dip oscillator.

In a further embodiment, the resilient mounting of the coil 5 and core 6 can comprise a body 8 of resilient material, such as silicone rubber gel, which extends between the front cover 2 and coil 5 as illustrated by dashed lines in the drawing. The body 8 does not contact the substantially cylindrical sides of coil 4 and preferably (as illustrated) does not contact the substantially cylindrical side of coil 5. The body 8 can be used alone, instead of, or in conjunction with, the membrane 7 for returning coil 5 to the rest position in the absence of added pressure on the core.

In a further embodiment, the resilient mounting for the coil 5 and core 6 can comprise two metal lever or leaf springs 10 and 11 (illustrated by dotted lines in the drawing) which are embedded in the housing 1 and which bear on the coil 5 and core 6.

In order to provide an absolute pressure measurement, the front cover 2 can be perforated or vented as at 9 and/or can be flexible thereby allowing uninhibited movement of the coil 5 and core 6. This absolute pressure measurement arrangement can be used for the rubber membrane 7 type of resilient mounting, the resilient material body 8 type of resilient mounting or the combination of the two types.

One advantage of the present invention is that the resonant frequency of the coils 4 and 5 may be measured remotely by the use of electro-magnetic or other fields without the need for external leads or wires to extend from the eye. Therefore the patient is not in any way confined nor is his mobility restricted as is the case with many prior art systems. In addition, the linear relationship between the transducer resonant frequency and intra-ocular pressure over physiological ranges results in highly desirable performance of the transducer. Furthermore the construction of the transducer is relatively uncomplicated and therefore the transducer is able to be constructed at low cost.

The foregoing describes only some embodiments of the present invention and modifications, obvious to those skilled in the art, may be made thereto without departing from the scope of the present invention.

What I claim is:

1. A miniature pressure transducer, comprising:
a container forming a housing;
an aperture in said container;
first and second parallel, planar, and co-axial coils arranged in proximity to one another in said container and having a common permeable core passing therethrough;
said core being axially aligned with said aperture;
said second coil being secured to a member fixed relative to said housing;
said first coil being secured to said core and movable therewith relative to said aperture, said fixed member and said coil; and resilient mounting means positioned between said core and said housing, supporting said core and said first coil for movement thereof relative to said fixed member and second coil without changing the volume within said container and maintaining said coils parallel and co-axial, and urging said core into a rest position relative to said fixed member and second coil in which one end of said core protrudes past said aperture;
said one end of said core being movable towards the interior of said container as said core moves from said rest position in response to a force applied to said one end of said core, said force being caused by pressure outside of said container whereby the change in spacing of said coils, and hence their remotely determinable resonant frequency, is directly proportional to a change in said outside pressure.

2. A transducer as claimed in claim 1, wherein:
said container comprises a cup-shaped cap adapted to be positioned on an eyeball;
said cup-shaped cap having a concave surface;
said fixed member forms part of said container and comprises an annular shelf centrally located on said concave surface of said cap; and
said aperture is centrally located in said shelf.

3. A transducer as claimed in claim 2, wherein:
said first coil is secured to the other end of said core; and
said second coil is interposed between said shelf and said first coil.

4. A transducer as claimed in claim 3, wherein:
said resilient mounting means comprises a membrane of resilient material secured to said shelf and said one end of said core, which membrane extends across and closes said aperture.

5. A transducer as claimed in claim 4, wherein:
said resilient material is selected from the group consisting of synthetic rubber and silicone rubber gel.

6. A transducer as claimed in claim 3, wherein:
said resilient mounting means comprises a body of resilient material interconnecting said first coil and the other end of said core with the interior of said container.

7. A transducer as claimed in claim 6, wherein:
said resilient material is selected from the group consisting of synthetic rubber and silicone rubber gel.

8. A transducer as claimed in claim 1, wherein:
said container includes vent means and the interior of said container communicates with the exterior of said container via said vent means.

9. An intra-ocular pressure transducer for the measurement of intra-ocular pressure in vivo, said transducer comprising:
a container forming a housing having an interior, and first and second co-axial coils and a co-axial substantially cylindrical permeable core therein;
said container comprising a cup-shaped cap having a concave surface adapted to be positioned on an eyeball, said concave surface having a central annular shelf with a central opening therethrough;
said core being located within said opening, having one end thereof extending through said opening and beyond said annular shelf, and having the other end thereof located interiorly of said container;
said first coil being secured to said other end of said core;
said second coil being secured to said annular shelf interiorly of said container, said coils being substantially planar and parallel; and
a mass of resilient material inter-connecting said core and said container, said core being longitudinally movable, in response to a force applied to said one end of said core by said eyeball, away from a rest position in which said coils abut each other to a position in which said coils are spaced apart but remain parallel to each other, said force being caused by pressure outside said container whereby the change in spacing of said coils, and hence their remotely determinable resonant frequency, is directly proportional to a change in said outside pressure.

10. A transducer as claimed in claim 9, wherein: said mass of resilient material comprises a membrane covering said opening and enveloping said one end of said core, the material of said membrane being selected from the group consisting of synthetic rubber and silicone rubber gel.

11. A transducer as claimed in claim 9, wherein: said mass of resilient material is disposed between the interior of said container and said other end of said core.

12. A transducer as claimed in claim 9, wherein: said container includes a vent communicating the interior of said container with the exterior of said container.

* * * * *